United States Patent
Snyder et al.

(10) Patent No.: US 8,616,464 B2
(45) Date of Patent: *Dec. 31, 2013

(54) PREFILMING ATOMIZER

(75) Inventors: Herman E Snyder, Pacifica, CA (US);
James Nasiatka, Berkeley, CA (US);
Christopher M Varga, Belmont, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/155,546

(22) Filed: Jun. 8, 2011

(65) Prior Publication Data

US 2011/0297755 A1    Dec. 8, 2011

Related U.S. Application Data

(63) Continuation of application No. 10/738,912, filed on Dec. 16, 2003, now Pat. No. 7,967,221.

(60) Provisional application No. 60/437,367, filed on Dec. 30, 2002.

(51) Int. Cl.
*B05B 7/06* (2006.01)

(52) U.S. Cl.
USPC ............ 239/8; 239/419.3; 239/421; 239/426; 239/429; 239/434; 239/543

(58) Field of Classification Search
USPC .................. 239/421, 426, 433, 434, 301, 418, 239/419.3, 422, 423, 425, 434.5, 293, 296, 239/400, 413–416.5, 429–431, 543–545, 8
See application file for complete search history.

(56) References Cited

U.S. PATENT DOCUMENTS

| | | | |
|---|---|---|---|
| 3,567,116 | A | 3/1971 | Lindlof |
| 3,770,207 | A | 11/1973 | Müller et al. |
| 3,790,079 | A | 2/1974 | Berglund et al. |
| 3,825,188 | A | 7/1974 | Doering |
| 3,980,233 | A | 9/1976 | Simmons et al. |
| 3,984,054 | A * | 10/1976 | Frochaux ............... 239/424 |
| 4,035,317 | A | 7/1977 | Gershberg |
| 4,052,255 | A | 10/1977 | Hackbarth et al. |

(Continued)

FOREIGN PATENT DOCUMENTS

| | | |
|---|---|---|
| EP | 0 072 046 | 2/1983 |
| EP | 0072046 | 2/1983 |

(Continued)

OTHER PUBLICATIONS

Bloch et al., "Dispersions of Hydrochlorothiazide and Chlorhalidone in Pentaerythritol." Pharm. Acta. Helv. (1983), 58 (1):, p. 14-22.

(Continued)

*Primary Examiner* — Jason Boeckmann
(74) *Attorney, Agent, or Firm* — Zilka-Kotab, PC

(57) ABSTRACT

A method of forming droplets comprises flowing a liquid through a channel; spreading the liquid into a thin film in the channel; and impinging the thin film with a flowing gas to atomize the liquid into droplets. The droplets may then be dried to produce dried particles, such as particles comprising a pharmaceutical active agent. The droplets formed by the disclosed process have improved size and/or size distribution characteristics.

6 Claims, 5 Drawing Sheets

(56) References Cited

U.S. PATENT DOCUMENTS

| | | | |
|---|---|---|---|
| 4,127,235 | A | 11/1978 | Klaile et al. |
| 4,221,339 | A | 9/1980 | Yoshikawa |
| 4,261,793 | A | 4/1981 | Nakamura et al. |
| 4,328,107 | A | 5/1982 | Wright |
| 4,361,281 | A | 11/1982 | Nash |
| 4,361,285 | A | 11/1982 | Koppehele et al. |
| 4,486,435 | A | 12/1984 | Schmidt et al. |
| 4,540,602 | A | 9/1985 | Motoyama et al. |
| 4,582,731 | A | 4/1986 | Smith |
| 4,590,206 | A | 5/1986 | Forrester et al. |
| 4,629,478 | A | 12/1986 | Browner et al. |
| 4,687,929 | A | 8/1987 | Browner et al. |
| 4,702,799 | A | 10/1987 | Tuot |
| 4,721,709 | A | 1/1988 | Seth et al. |
| 4,742,810 | A | 5/1988 | Anders et al. |
| 4,748,034 | A | 5/1988 | de Rham |
| 4,760,093 | A | 7/1988 | Blank et al. |
| 4,762,995 | A | 8/1988 | Browner et al. |
| 4,784,878 | A | 11/1988 | Haak |
| 4,794,167 | A | 12/1988 | Lindner et al. |
| 4,807,814 | A | 2/1989 | Douche et al. |
| 4,818,424 | A | 4/1989 | Evans et al. |
| 4,835,187 | A | 5/1989 | Reuter et al. |
| 4,871,489 | A | 10/1989 | Ketcham |
| 4,919,853 | A | 4/1990 | Alvarez et al. |
| 4,924,097 | A | 5/1990 | Browner et al. |
| 4,952,402 | A | 8/1990 | Sparks et al. |
| 4,970,093 | A | 11/1990 | Sievers et al. |
| 4,977,785 | A | 12/1990 | Willoughby et al. |
| 5,000,888 | A | 3/1991 | Kilbride, Jr. et al. |
| 5,009,367 | A | 4/1991 | Nielsen |
| 5,015,423 | A | 5/1991 | Eguchi et al. |
| 5,017,372 | A | 5/1991 | Hastings |
| 5,026,550 | A | 6/1991 | Aeschbach et al. |
| 5,064,501 | A | 11/1991 | Boersen |
| 5,076,097 | A | 12/1991 | Zarrin et al. |
| 5,106,659 | A | 4/1992 | Hastings et al. |
| 5,115,971 | A | 5/1992 | Greenspan et al. |
| 5,160,664 | A | 11/1992 | Liu |
| 5,175,433 | A | 12/1992 | Browner et al. |
| 5,219,120 | A | 6/1993 | Ehrenberg et al. |
| 5,221,731 | A | 6/1993 | Weymans et al. |
| 5,247,842 | A | 9/1993 | Kaufman et al. |
| 5,248,087 | A | 9/1993 | Dressler |
| 5,260,306 | A | 11/1993 | Boardman et al. |
| 5,269,980 | A | 12/1993 | Levendis et al. |
| 5,279,708 | A | 1/1994 | Wood et al. |
| 5,309,900 | A | 5/1994 | Knoch et al. |
| 5,376,386 | A | 12/1994 | Ganderton et al. |
| 5,384,133 | A | 1/1995 | Boyes et al. |
| 5,437,798 | A | 8/1995 | LaRoche et al. |
| 5,482,927 | A | 1/1996 | Maniar et al. |
| 5,500,027 | A | 3/1996 | Rudolph et al. |
| 5,518,709 | A | 5/1996 | Sutton et al. |
| 5,542,935 | A | 8/1996 | Unger et al. |
| 5,560,543 | A | 10/1996 | Smith et al. |
| 5,573,392 | A | 11/1996 | Paikert et al. |
| 5,580,237 | A | 12/1996 | Leger |
| 5,580,856 | A | 12/1996 | Prestrelski et al. |
| 5,607,697 | A | 3/1997 | Alkire et al. |
| 5,609,919 | A | 3/1997 | Yuan et al. |
| 5,622,657 | A | 4/1997 | Takada et al. |
| 5,624,530 | A | 4/1997 | Sadykhov et al. |
| 5,628,937 | A | 5/1997 | Oliver et al. |
| 5,639,441 | A | 6/1997 | Sievers et al. |
| 5,648,096 | A | 7/1997 | Gander et al. |
| 5,651,990 | A | 7/1997 | Takada et al. |
| 5,667,806 | A | 9/1997 | Kantor |
| 5,687,905 | A | 11/1997 | Tsai |
| 5,709,886 | A | 1/1998 | Bettman et al. |
| 5,716,558 | A | 2/1998 | Nielsen et al. |
| 5,723,269 | A | 3/1998 | Akagi et al. |
| 5,727,333 | A | 3/1998 | Folan |
| 5,732,885 | A | 3/1998 | Huffman |
| 5,740,966 | A | 4/1998 | Blaha-Schnabel |
| 5,741,478 | A | 4/1998 | Osborne et al. |
| 5,770,559 | A | 6/1998 | Manning et al. |
| 5,776,491 | A | 7/1998 | Allen, Jr. et al. |
| 5,785,049 | A | 7/1998 | Smith et al. |
| 5,795,594 | A | 8/1998 | York et al. |
| 5,800,598 | A | 9/1998 | Chein et al. |
| 5,807,576 | A | 9/1998 | Allen, Jr. et al. |
| 5,845,846 | A | 12/1998 | Watanabe et al. |
| 5,851,453 | A | 12/1998 | Hanna et al. |
| 5,855,913 | A | 1/1999 | Hanes et al. |
| 5,874,029 | A | 2/1999 | Subramaniam et al. |
| 5,874,064 | A | 2/1999 | Edwards et al. |
| 5,922,675 | A | 7/1999 | Baker et al. |
| 5,924,216 | A | 7/1999 | Takahashi |
| 5,934,566 | A * | 8/1999 | Kanno et al. .................. 239/398 |
| 5,938,117 | A | 8/1999 | Ivri |
| 5,957,848 | A | 9/1999 | Sutton et al. |
| 5,964,416 | A | 10/1999 | Jaeger et al. |
| 5,970,974 | A | 10/1999 | VanDerLinden et al. |
| 5,972,388 | A | 10/1999 | Sakon et al. |
| 5,976,574 | A | 11/1999 | Gordon |
| 5,981,474 | A | 11/1999 | Manning et al. |
| 5,985,248 | A | 11/1999 | Gordon et al. |
| 5,985,309 | A | 11/1999 | Edwards et al. |
| 5,993,805 | A | 11/1999 | Sutton et al. |
| 5,997,848 | A | 12/1999 | Patton et al. |
| 6,000,241 | A | 12/1999 | Ranade et al. |
| 6,001,336 | A | 12/1999 | Gordon |
| 6,014,970 | A | 1/2000 | Ivri et al. |
| 6,015,546 | A | 1/2000 | Sutton et al. |
| 6,017,310 | A | 1/2000 | Johnson et al. |
| 6,022,525 | A | 2/2000 | Sutton et al. |
| 6,051,256 | A * | 4/2000 | Platz et al. .................... 424/489 |
| 6,051,257 | A | 4/2000 | Kodas et al. |
| 6,063,138 | A | 5/2000 | Hanna et al. |
| 6,077,543 | A | 6/2000 | Gordon et al. |
| 6,090,407 | A | 7/2000 | Knight et al. |
| 6,116,516 | A | 9/2000 | Ganan-Calvo |
| 6,117,455 | A | 9/2000 | Takada et al. |
| 6,119,953 | A | 9/2000 | Ganan-Calvo et al. |
| 6,136,295 | A | 10/2000 | Edwards et al. |
| 6,149,941 | A | 11/2000 | Schwarz et al. |
| 6,174,469 | B1 | 1/2001 | Ganan-Calvo |
| 6,197,835 | B1 | 3/2001 | Ganan-Calvo |
| 6,223,455 | B1 | 5/2001 | Chickering, III et al. |
| 6,241,159 | B1 | 6/2001 | Ganan-Calvo et al. |
| 6,258,341 | B1 | 7/2001 | Foster et al. |
| 6,290,991 | B1 | 9/2001 | Roser et al. |
| 6,308,434 | B1 | 10/2001 | Chickering, III et al. |
| 6,316,029 | B1 | 11/2001 | Jain et al. |
| 6,331,290 | B1 | 12/2001 | Morgan |
| 6,331,310 | B1 | 12/2001 | Roser et al. |
| 6,352,209 | B1 | 3/2002 | Skeath et al. |
| 6,365,190 | B1 | 4/2002 | Gordon et al. |
| 6,383,810 | B2 | 5/2002 | Fike et al. |
| 6,416,739 | B1 | 7/2002 | Rogerson et al. |
| 6,423,344 | B1 | 7/2002 | Platz et al. |
| 6,451,349 | B1 | 9/2002 | Robinson et al. |
| 6,503,480 | B1 | 1/2003 | Edwards et al. |
| 6,565,885 | B1 | 5/2003 | Tarara et al. |
| 6,572,893 | B2 | 6/2003 | Gordon et al. |
| 6,582,728 | B1 | 6/2003 | Platz et al. |
| 6,592,904 | B2 | 7/2003 | Platz et al. |
| 6,656,492 | B2 | 12/2003 | Kajiyama et al. |
| 6,860,907 | B1 | 3/2005 | Hanna et al. |
| 7,004,181 | B2 | 2/2006 | Isago et al. |
| 2002/0071871 | A1 | 6/2002 | Snyder et al. |
| 2002/0081266 | A1 | 6/2002 | Woolfe et al. |
| 2002/0175225 | A1* | 11/2002 | Boersen et al. ................ 239/506 |
| 2003/0047824 | A1 | 3/2003 | Hanna et al. |
| 2003/0109421 | A1 | 6/2003 | Palakodaty et al. |
| 2003/0124193 | A1 | 7/2003 | Snyder et al. |
| 2003/0203036 | A1 | 10/2003 | Gordon et al. |
| 2003/0215514 | A1 | 11/2003 | Platz et al. |
| 2004/0119179 | A1 | 6/2004 | Perrut et al. |
| 2005/0206023 | A1 | 9/2005 | Hanna et al. |

(56) References Cited

U.S. PATENT DOCUMENTS

FOREIGN PATENT DOCUMENTS

| | | |
|---|---|---|
| EP | 0344375 | 12/1989 |
| EP | 0408801 | 1/1991 |
| EP | 455892 | 11/1991 |
| EP | 0461930 | 12/1991 |
| EP | 469725 | 2/1992 |
| EP | 512693 | 11/1992 |
| EP | 0611567 | 8/1994 |
| EP | 628331 | 12/1994 |
| EP | 746751 | 2/1995 |
| EP | 674541 | 10/1995 |
| EP | 681843 | 11/1995 |
| EP | 709085 | 5/1996 |
| EP | 899017 | 3/1999 |
| EP | 972526 | 1/2000 |
| EP | 1 004 349 | 5/2000 |
| GB | 473471 | 10/1937 |
| GB | 621785 | 4/1949 |
| GB | 2 105 189 | 3/1983 |
| GB | 2105189 | 3/1983 |
| GB | 2322326 | 8/1998 |
| GB | 0300338.1 | 1/2003 |
| GB | 0300339.9 | 1/2003 |
| WO | WO 88/07870 | 10/1988 |
| WO | WO 89/05196 | 6/1989 |
| WO | WO 90/11139 | 10/1990 |
| WO | WO 91/16882 | 11/1991 |
| WO | WO 92/18164 | 10/1992 |
| WO | WO 93/07465 | 4/1993 |
| WO | WO 94/08627 | 4/1994 |
| WO | WO 95/01221 | 1/1995 |
| WO | WO 95/01324 | 1/1995 |
| WO | WO 95/13864 | 5/1995 |
| WO | 95/24183 | 9/1995 |
| WO | WO 95/23613 | 9/1995 |
| WO | WO 95/31479 | 11/1995 |
| WO | WO 96/00610 | 1/1996 |
| WO | WO 96/03978 | 2/1996 |
| WO | WO 96/05809 | 2/1996 |
| WO | 96/09814 | 4/1996 |
| WO | WO 96/11580 | 4/1996 |
| WO | WO 96/15814 | 5/1996 |
| WO | 96/32149 | 10/1996 |
| WO | WO 96/32096 | 10/1996 |
| WO | WO 97/14407 | 4/1997 |
| WO | WO 97/28788 | 8/1997 |
| WO | WO 97/31691 | 9/1997 |
| WO | WO 97/36574 | 10/1997 |
| WO | WO 97/36578 | 10/1997 |
| WO | 97/41833 | 11/1997 |
| WO | WO 97/44067 | 11/1997 |
| WO | WO 98/01228 | 1/1998 |
| WO | WO 98/17676 | 4/1998 |
| WO | WO 98/29096 | 7/1998 |
| WO | WO 98/29098 | 7/1998 |
| WO | WO 98/31346 | 7/1998 |
| WO | WO 98/36825 | 8/1998 |
| WO | WO 98/36888 | 8/1998 |
| WO | WO 98/47493 | 10/1998 |
| WO | 99/16419 | 4/1999 |
| WO | 99/16422 | 4/1999 |
| WO | WO 99/17748 | 4/1999 |
| WO | WO 99/30834 | 6/1999 |
| WO | WO 99/31019 | 6/1999 |
| WO | WO 99/32083 | 7/1999 |
| WO | WO 99/44733 | 9/1999 |
| WO | WO 99/59710 | 11/1999 |
| WO | WO 00/00176 | 1/2000 |
| WO | WO 00/09084 | 2/2000 |
| WO | WO 00/10541 | 3/2000 |
| WO | WO 00/12278 | 3/2000 |
| WO | WO 00/13668 | 3/2000 |
| WO | WO 00/66256 | 11/2000 |
| WO | 00/78447 | 12/2000 |
| WO | WO 00/76673 | 12/2000 |
| WO | WO 01/03673 | 1/2001 |
| WO | WO 01/03821 | 1/2001 |
| WO | WO 01/13885 | 3/2001 |
| WO | WO 01/15664 | 3/2001 |
| WO | WO 01/45731 | 6/2001 |
| WO | WO 01/64188 | 9/2001 |
| WO | WO 01/87278 | 11/2001 |
| WO | 02/09669 | 2/2002 |
| WO | WO 02/15876 | 2/2002 |
| WO | Wo 02/15880 | 2/2002 |
| WO | WO 02/32462 | 4/2002 |
| WO | WO 02/078675 | 10/2002 |
| WO | WO 03/000202 | 1/2003 |
| WO | WO 03/008082 | 1/2003 |
| WO | 2004/007085 | 1/2004 |

OTHER PUBLICATIONS

Bohnet. Matthias, "Calculation and Design of Gas/Solid-Injectors," Powder Tech, 1984, pp. 302-313.
Carpenter, John F. et al., "Modes of Stabilization of a Protein by Organic Solutes During Desiccation," Cryobiology. 1988. vol. 25, pp. 459-470.
Jung et al., "Particle Design Using Supercritical Fluids: Literature and Patent Survey." J. of Supercritical Fluids vol. 20. n. 179-219 (2001).
Mohamed et al., "Solids Formation After the Expansion of Supercritical Mixtures." Supercritical Fluid Science and Technology. Chapter 23. American Chemical Society, p. 355-378 (1989).
Mumenthaler et al., "Feasibility Study on Spray-Drying Protein Pharmaceutical: Recombinant Human Growth Hormaoine and Tissue-Type Plasminogen Activator." Pharm Res. (1994), 11(1):, p. 12-20.
Witham, Clyde L., "Dry Dispersion With Sonic Velocity Nozzles," Workshop on Dissemination Techniques for Smoke and Obscurants Chemical Systems Laboratory. Aberdeen Proving Group, MD, Mar. 14-16, 1983, pp. 1-26.

Benjamin, "Fuel Atomization for Next-Generation Gas Turbine Combustors", Atomization and Sprays (2000), vol. 10, pp. 427-438.

Hino et al., "Development of a new type nozzle and spray-drier for industrial production of fine powders", European J. of Pharmaceutics and Biopharmaceutics (2000), vol. 49, pp. 79-85.

Dunbar Ca et al "Evaluation of Atomizer Performance in Production of Respirable Spray-Dried Particles" *Pharm Dev Technol* 3(4):433-441 (1998).

International Search Report, PCT/US03/40166 (Aug. 11, 2004).

Written Opinion, PCT/US03/40166 (Aug. 17, 2004).

He et al., "Chitosan Microspheres Prepared by Spray Drying" International J. of Pharm. (Amsterdam), vol. 187, No. 1, p. 53-65 (1999).

Lefebvre, "Atomization and Sprays", Combustion: An International Series, Chigier Norman ed., Taylor & Francis, pp. 140-142 and pp. 193-196 (1989).

Masters K, "The Process Stages of Spray Drying: Pneumatic (Two-Fluid) Atomization", Spray Drying Handbook, 5th ed, John Wiley & Sons, 6.6.3, pp. 250-267 (1991).

* cited by examiner

PREFILMING ATOMIZER

This is a continuation of U.S. patent application Ser. No. 10/738,912 (pending) filed on Dec. 16, 2003, which claims the benefit of U.S. Provisional Patent Application Ser. No. 60/437,367 filed on Dec. 30, 2002, which is incorporated herein by reference in its entirety.

BACKGROUND

The ability to accurately and reproducibly produce particles having a well defined particle size and particle size distribution from a liquid feed stock has application in a variety of fields, including food, chemicals, and pharmaceuticals. Such control of particle size and particle size distribution is particularly important in pharmaceutical applications where liquid or dry powder particles containing an active agent are administered to a patient. Controlling the particle size and particle size distribution is desirable in such applications in order to achieve delivery of such particles in a known and repeatable manner.

Powders for pharmaceutical drug administration have been made by spray drying. Spray drying is a conventional chemical processing unit operation used in the chemical, food, and pharmaceutical industries to produce dry particulate solids from a variety of liquid and slurry materials. The process involves rapidly transforming a liquid feed into a dried particulate form by atomizing the feed into a hot drying medium.

Conventional spray drying systems and processes have been disclosed. For example, U.S. Pat. Nos. 5,260,306, 4,590,206, GB 2,105,189, and EP 072 046 describe a method for spray drying nedocromil sodium to form small particles preferably in the range from 2-15 mm for pulmonary delivery. U.S. Pat. No. 5,376,386 describes the preparation of particulate polysaccharide carriers for pulmonary drug delivery, where the carriers comprise particles sized from 5-100 mm and having a rugosity of less than 1.75. WO 96/09814 discloses spray-dried smooth and spherical microparticles which either carry a therapeutic or diagnostic agent. U.S. Pat. No. 6,022,525 discloses microcapsules prepared by spray-drying and which are useful for ultrasonic imaging. Additionally, aerodynamically light particles for pulmonary delivery and particles incorporating surfactants for pulmonary drug delivery and their preparation are disclosed in U.S. Pat. Nos. 5,855,913 and 5,874,064. The spray drying of hydrophobic drugs and excipients is disclosed in U.S. Pat. Nos. 5,976,574, 5,985,248, 6,001,336, and 6,077,543. U.S. Provisional Patent Application 60/222,067 filed on Aug. 1, 2000 discloses a spray drying process that can be tailored to produce substantially monodisperse particles or multimodal particles having well defined and controllable particle size distributions. Additional spray drying processes are disclosed in EP 1004349, WO 96/32149, WO 99/16419, and U.S. Pat. Nos. 6,000,241, and 6,051,256, and in The Spray Drying Handbook, K. Masters. All of the aforementioned references are incorporated herein by reference in their entireties. Various atomizers have been used in the spray drying of pharmaceutical powders. These include gas assisted two fluid nozzles, rotary atomizers and ultrasonic atomizers comprising an oscillating horn to create surface instabilities resulting in droplet formation. Examples of each of these various atomizers are disclosed in the patents cited above. Droplet size and droplet size distribution are affected by the selection of the atomizer.

The application of conventional spray drying technology to the field of pulmonary drug administration presents many technical challenges. For example, there are often particular sizing requirements necessary to administer resultant particles to the deep lung. For pulmonary applications, the aerodynamic size of the particles dispersed in an aerosol directly impacts the deposition pattern in the lung. The major factors influencing this final particle size include the initial liquid drop size, the initial solids concentration, and the drying rate. It is advantageous to create small liquid droplets with the highest solids concentration feasible for a particular process to minimize capital equipment and operating costs.

It can be difficult to achieve a desired low moisture content required for physical and chemical stability in the final particulate product, particularly in an economic manner. Finally, it has proven to be difficult to produce the small particles necessary for some pharmaceutical applications, such as pulmonary delivery, in an efficient manner on a large scale suitable for commercial applications.

Therefore, it is desirable to be able to produce spray dried particles in an improved manner. It is further desirable to be able to produce spray dried particles within a narrow size distribution, in particular for pulmonary drug administration. It is further desirable to be able to generate desired particles in an economic manner.

SUMMARY

The present invention satisfies these needs. In one aspect of the invention, an atomizer forms liquid into a thin film for the production of droplets having improved characteristics.

In one aspect of the invention, a method of forming droplets comprises flowing a liquid through a channel; spreading the liquid into a thin film in the channel; and impinging the thin film with a flowing gas to atomize the liquid into droplets.

In one aspect of the invention, a method of forming droplets comprises flowing a liquid through a channel; spreading the liquid into a thin film in the channel; and impinging the thin film with a flowing gas to atomize the liquid into droplets having a diameter less than 35 micrometers.

In another aspect of the invention, a method of forming comprises flowing a liquid through a channel; spreading the liquid into a thin film; and impinging the thin film with a flowing gas to atomize the liquid into droplets, the flowing gas impinging the thin film at a right angle.

In another aspect of the invention, a method of forming a pharmaceutical formulation comprises flowing a liquid through a channel, the liquid comprising a pharmaceutical active agent; spreading the liquid into a thin film; impinging the thin film with a flowing gas to atomize the liquid into droplets; and drying the droplets to form particles comprising the active agent.

In another aspect of the invention, a pharmaceutical formulation is produced by a method comprising flowing a liquid through a channel, the liquid comprising a pharmaceutical active agent; spreading the liquid into a thin film; impinging the thin film with a flowing gas to atomize the liquid into droplets; and drying the droplets to form particles comprising the active agent.

In another aspect of the invention, an atomizer for forming droplets comprises a first channel through which a liquid may flow, the channel comprising a constriction for spreading the liquid into a thin film in the channel; and a second channel though which an atomizing gas may flow, the second channel being positioned so that the atomizing gas impinges the liquid thin film in a manner which produces droplets having a diameter less than 35 micrometers.

In another aspect of the invention, an atomizer for forming comprises a first channel through which a liquid may flow, the channel comprising a constriction for spreading the liquid into a thin film in the channel; and a second channel though which an atomizing gas may flow, the second channel being positioned so that the atomizing gas impinges the liquid thin film at a right angle to produce droplets.

In another aspect of the invention, a spray drying system for forming a pharmaceutical formulation comprises an atomizer, the atomizer comprising a first channel through which a liquid may flow, the channel comprising a constriction for spreading the liquid into a thin film in the channel, the atomizer further comprising a second channel though which an atomizing gas may flow, the second channel being positioned so that the atomizing gas impinges the liquid thin film to produce droplets; a drying chamber to dry the droplets; and a collector to collect particles dried in the chamber.

DRAWINGS

These features, aspects, and advantages of the present invention will become better understood with regard to the following description, appended claims, and accompanying drawings which illustrate exemplary features of the invention. However, it is to be understood that each of the features can be used in the invention in general, not merely in the context of the particular drawings, and the invention includes any combination of these features, where:

DESCRIPTION

The present invention is directed to the formation of droplets. In particular, the invention is directed to the formation of droplets for forming spray dried particles from a liquid feed stock. Although the process is illustrated in the context of producing pharmaceutical particles for pulmonary administration, the present invention can be used in other pharmaceutical or non-pharmaceutical processes and should not be limited to the examples provided herein.

Figure 1:
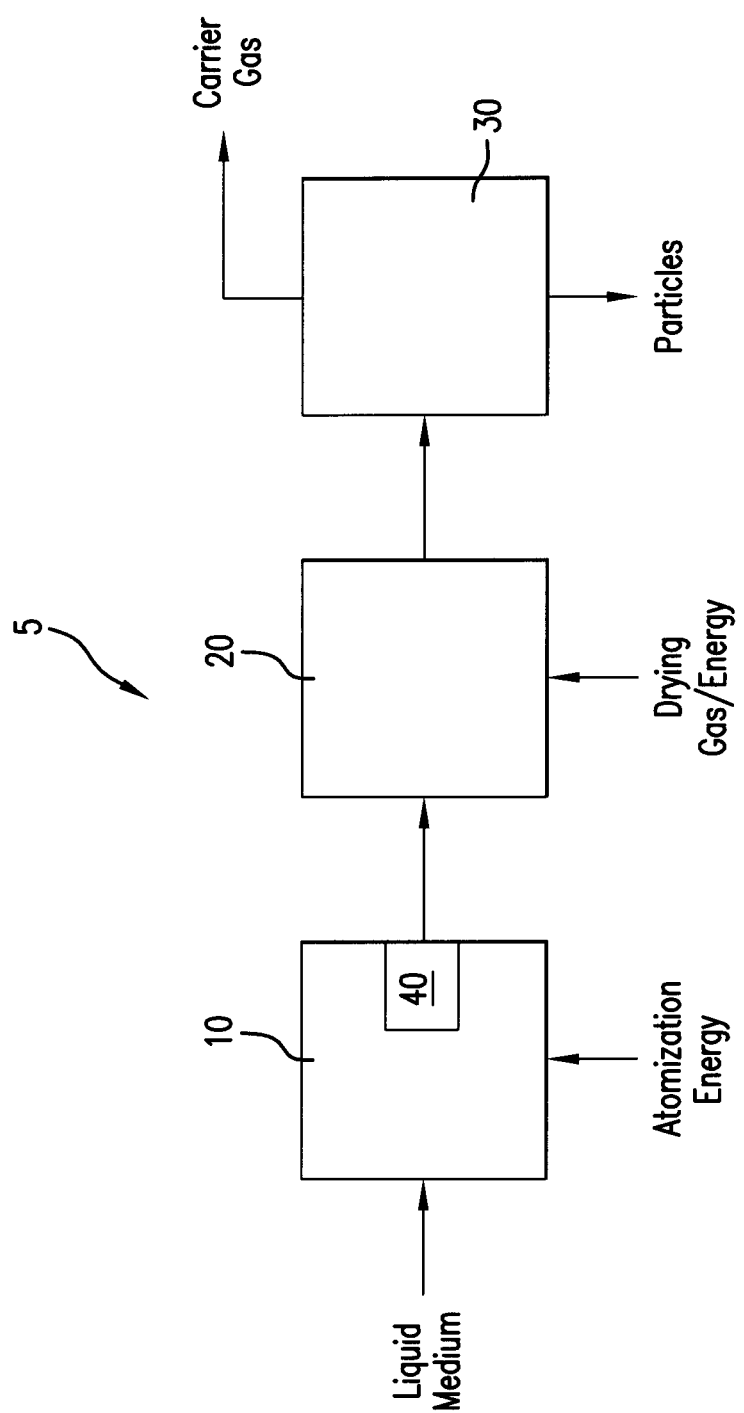
FIG. 1 is a schematic of a spray drying process according to the invention.

A spray drying system 5 according to the invention is shown in FIG. 1. The spray drying system 5 comprises an atomization operation 10 which produces droplets of a liquid medium which are dried in a drying operation 20. Drying of the liquid droplets results in formation of the discrete particles which form the dry powder compositions which are then collected in a separation operation 30. In one version, the components of the spray drying system may be as described in U.S. Provisional Patent Application Ser. No. 60/222,067 filed on Aug. 1, 2000 and in U.S. Pat. No. 6,051,256, both of which are incorporated herein by reference in their entireties. In the spray drying system 5 of FIG. 1, the atomization operation is performed by an atomizer 40 that spreads a liquid into a film and then impinges the liquid with a gas to form droplets.

Figure 2:
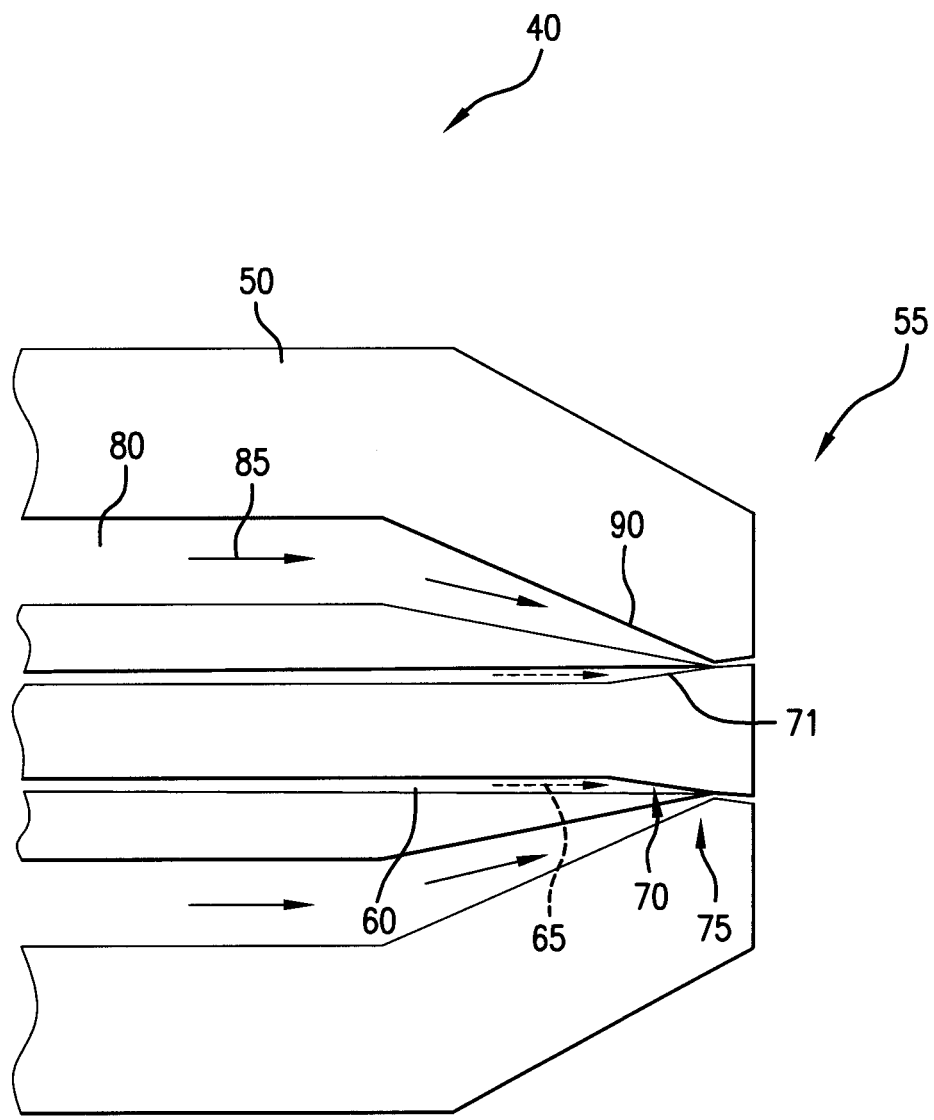
FIG. 2 is a schematic sectional side view of a version of an atomizer according to the invention.

A version of an atomizer 40 according to the invention is shown in FIG. 2. The atomizer 40 comprises a housing 50 that defines a nozzle 55 by which a liquid feedstock may be atomized into droplets. In this version, the housing 50 comprises a first annular channel 60 through which the liquid feed stock 65 flows. A forward portion 70 of the first annular channel 60 narrows to a constricted portion 71 which serves to form the liquid feed stock flowing through the first annular channel 60 into a thin annular film. In the version shown, the thin film is created by a expanding conical surface at the forward portion 70. The thin annular film of liquid feed stock exits the first annular channel 60 at a forward end 75 of the first annular channel 60. A second annular channel 80 is provided for the transport of atomization gas 85. The second annular channel 80 is shaped at its forward end 90 so that at a high speed, such as sonic velocity, the atomization gas annulus impinges against the thin annular film of the liquid feedstock.

The impingement of the atomization gas annulus onto the this annular film of liquid in the version of FIG. 2 provides improved droplet formation. The droplets are formed by using the atomization gas annulus to pull droplets off the edge of the expanding conical surface at the forward end 70 of the first annular channel 60. By both thinning the liquid and increasing the amount of surface area per unit volume of liquid for interaction with the atomization gas, the efficiency of atomization is improved. This allows for smaller droplet sizes to be created using less atomization gas. The thickness of the thin film allows for the formation of desired droplets. In one version, the thin film is less than 0.020 in, more preferably less than 0.005 in, more preferably less than 0.002 in, and most preferably about 0.001 in. It has also been determined that by forming the thin film by nature of the shape of the channel and then impinging the thin film with a gas, the size distribution of the droplets formed is within a narrower range and is more controllable.

Figure 3:
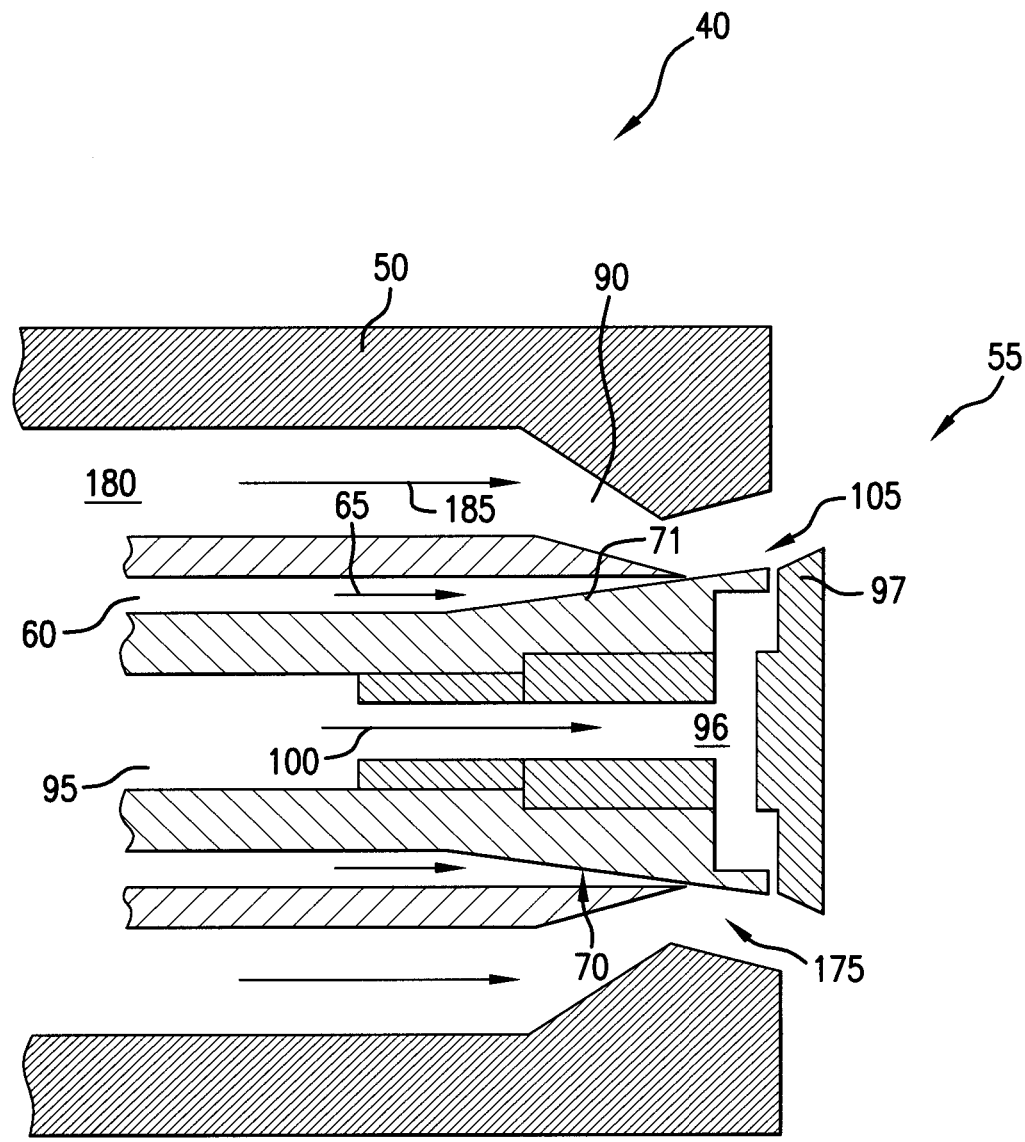
FIG. 3 is a schematic sectional side view of another version of an atomizer according to the invention.

Another version of an atomizer 40 is shown in FIG. 3. In this version, the atomizer comprises a first annular channel 60 through which a liquid feed stock 65 flows. In this version, the liquid feedstock is shaped into a thin film using a constricted portion 71, as in the version of FIG. 2. A second annular channel 180 is provided through which a gas 185 flows to contact the thin film from the first annular channel 60 at a contact point 175. In addition, a third channel 95 provides an atomization gas 100. The third channel 95 is shaped at its forward end 96 so that a the gas is redirected through a thin opening 97 so that a thin stream of atomization gas impinges the thin annular film of liquid at an impingement point 105. In the version shown, the impingement point 105 is downstream from the contact point 175. The impingement of the liquid thin film and the redirected atomization gas produces droplets of a desirable character. The second annular channel 180 may be designed so that the gas therein impinges the thin film of the liquid feedstock to also produce droplets and/or may serve to aid in the transport of the thin film to the impingement point 105. In this way, this version offers improved atomization efficiency by providing a backing against which the thin film of liquid may be impinged by the atomization gas from the opening 97. In an alternative version, the second annular channel 180 may be removed.

Figure 4:
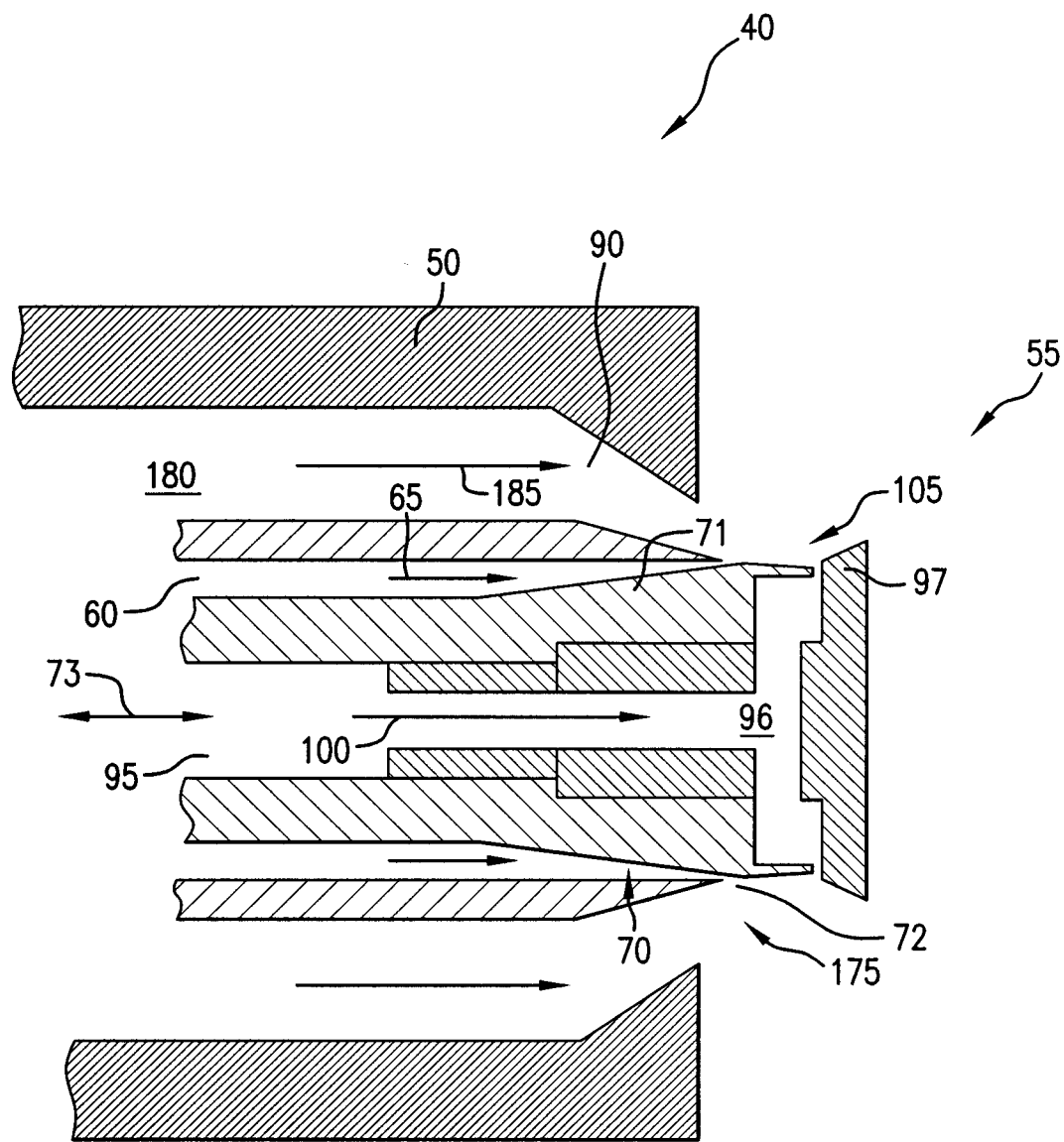
FIG. 4 is a schematic sectional side view of another version of an atomizer according to the invention.

Another version of an atomizer 40 is shown in FIG. 4. The version of FIG. 4 is similar to the version of FIG. 3. However, in the version of FIG. 4, the forward end 70 of the first channel 60 is shaped 72 so the thin film exits the first channel 60 in a direction that is parallel to the elongated axis 73 of the atomizer 40. In the version of FIG. 4, the thin film is cylindrically shaped from the forward portion 70 to the impingement point 105. With this shape, the atomization gas exiting the opening 97 impinges the thin film at a right angle thereto. This provides improved control over the droplet formation.

Figure 5:
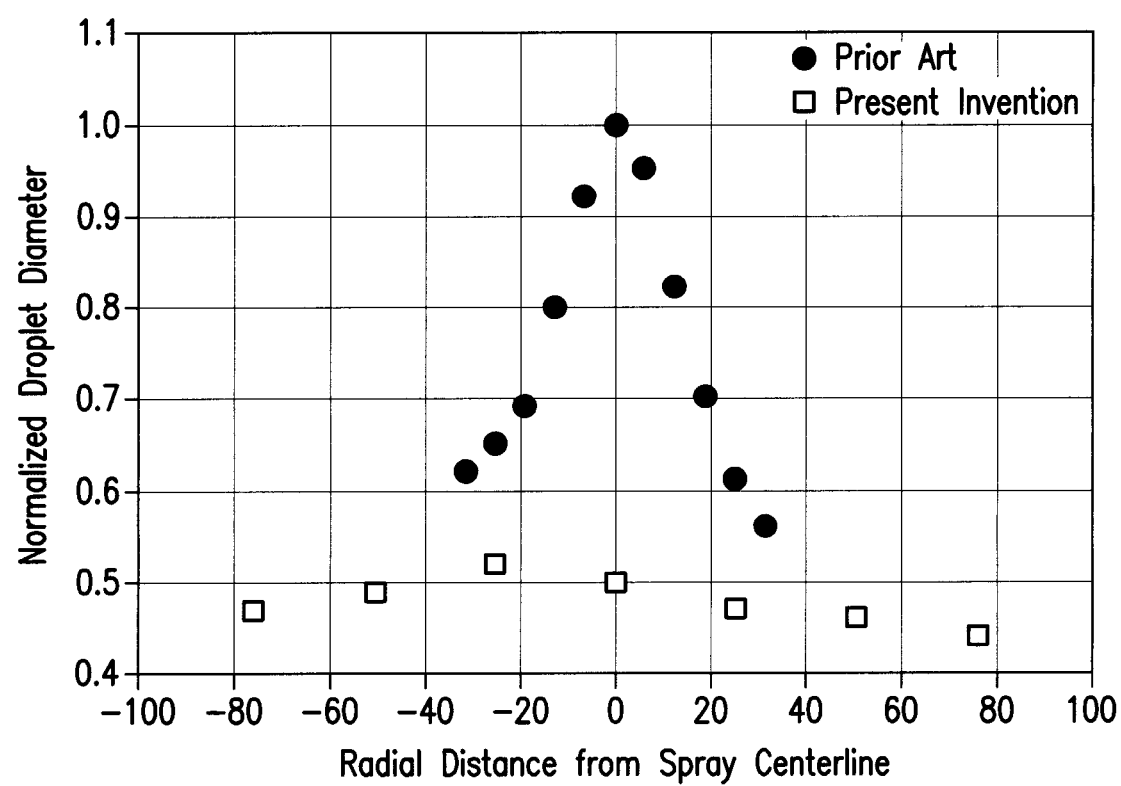
FIG. 5 is a graph showing normalized droplet diameter as a function of radial distance from the centerline of an atomizer according to the invention in comparison with a prior art atomizer.

The atomizer 40 according to the invention provides significantly improved atomization efficiency and allows for the ability to create smaller and more uniform liquid droplet sizes. For example, droplets less than 35 microns, and preferably less than 10 microns may be generated. The advantage of smaller droplet sizes is that a smaller final particle size for a given solid concentration may be obtained. Alternatively, a solid concentration may be increased while maintaining a particular particle size. This would allow for increased system throughput. The increased size distribution is shown in FIG. 5. FIG. 5 shows a graph of droplet diameter as a function of radial distance from the centerline of the atomizer for both the atomizer 40 of FIG. 4 and a prior art atomizer of U.S. Pat. No. 6,051,256. As can be seen, the droplet diameter is significantly more uniform and smaller for the atomizer 40 of the present invention.

The atomizer 40 according to the invention also allows for particular control over the atomization process. For example, by adjusting the mass flow ratios of the inner to the outer streams, the angle of the droplet spray can be adjusted. Accordingly, the spray can be optimized for a particular spray drying system. In addition, the optimization of the spray cone angle can minimize the droplet number density across the spray and provide a more uniform droplet drying process with more uniform particle characteristics. Particles produced by spray drying a liquid feed stock may be produced in order to produce a desired particle size and particle size distribution of the spray dried particles. Accordingly, spray dried particles can be produced having a desired median diameter and particle size distribution resulting solely from the spray drying process. Further separation processing, such as filtration or centrifugation and the like, may or may not be present and is often not necessary to provide the desired particle size distribution. Control of particles size and particle size distribution of the present invention can be used in combination with control over other process parameters, such as drying rate, to provide even more control over particle morphology.

In order to control the final moisture content of the particles produced in the drying operation, it is desirable to also control the gas outlet temperature and or relative humidity. The gas outlet temperature will be a function of the inlet temperature, the heat load imposed by the product drying step (which depends on the inlet temperature of the liquid medium, the quantity of water to be evaporated, and the like), and other factors. Preferably the gas outlet temperature will be maintained at least 50° C. or above, preferably at least 70° C., usually in the range from 60-80° C.

The drying operation may be controlled to provide dried particles having particular characteristics, such as a rugosity above 2 as described in WO 97/41833, which is incorporated herein by reference in its entirety. The drying rate may be controlled by a number of variables, including the droplet size distribution, the inlet temperature of the gas stream, the outlet temperature of the gas stream, the inlet temperature of the liquid droplets, and the manner in which the atomized spray and drying gas are mixed. Preferably, the drying gas stream will have an inlet temperature of at least 90° C., preferably at least 120° C., and more preferably at least 135° C., and still more preferably at least 145° C. and often 175-200° C. depending upon the particular active agent being treated.

In one version, the spray drying process 5 may be used to form low density particles, such as particles having a density below 0.5 g/cm$^3$. For example, the feedstock may comprise a lipid, such as a phospholipid, and an active agent to produce particles where the active agent is contained within a lipid matrix. Additionally or alternatively, the feedstock may include a blowing agent for the production of hollow and/or porous particles, as described for example in WO99/16419 which is incorporated herein by reference in its entirety.

The methods of the present invention are useful for producing particles of pharmaceutical agents such as proteins, polypeptides, oligopeptides, nucleic acids, and the like. The method is useful for the production of particles of a size suitable for pulmonary administration, and is particularly useful for the production of insulin particles for pulmonary delivery.

Accordingly, in one version, the spray dry system 5 provides a pharmaceutical formulation comprising particles that may be a aerosolized and delivered to the respiratory tract of the user, and in particular to the alveolar regions of the lungs of the user. The pharmaceutical formulation may comprise powdered medicaments, liquid solutions or suspensions, and the like, and may include an active agent.

The active agent described herein includes an agent, drug, compound, composition of matter or mixture thereof which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. An active agent for incorporation in the pharmaceutical formulation described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable active agents may be selected from, for example, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition).

The amount of active agent in the pharmaceutical formulation will be that amount necessary to deliver a therapeutically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1% by weight to about 99% by weight active agent, typically from about 2% to about 95% by weight active agent, and more typically from about 5% to 85% by weight active agent, and will also depend upon the relative amounts of additives contained in the composition. The compositions of the invention are particularly useful for active agents that are delivered in doses of from 0.001 mg/day to 100 mg/day, preferably in doses from 0.01 mg/day to 75 mg/day, and more preferably in doses from 0.10 mg/day to 50 mg/day. It is to be understood that more than one active agent may be incorporated into the formulations described herein and that the use of the term "agent" in no way excludes the use of two or more such agents.

The pharmaceutical formulation may comprise a pharmaceutically acceptable excipient or carrier which may be taken into the lungs with no significant adverse toxicological effects to the subject, and particularly to the lungs of the subject. In addition to the active agent, a pharmaceutical formulation may optionally include one or more pharmaceutical excipients which are suitable for pulmonary administration. These excipients, if present, are generally present in the composition in amounts ranging from about 0.01% to about 95% percent by weight, preferably from about 0.5 to about 80%, and more preferably from about 1 to about 60% by weight. Preferably, such excipients will, in part, serve to further improve the features of the active agent composition, for example by providing more efficient and reproducible delivery of the active agent, improving the handling characteristics of powders, such as flowability and consistency, and/or facilitating manufacturing and filling of unit dosage forms. In particular, excipient materials can often function to further improve the physical and chemical stability of the active agent, minimize the residual moisture content and hinder moisture uptake, and to enhance particle size, degree of aggregation, particle surface properties, such as rugosity, ease of inhalation, and the targeting of particles to the lung. One or more excipients may also be provided to serve as bulking agents when it is desired to reduce the concentration of active agent in the formulation.

Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination. Suitable excipients are those provided in WO 96/32096, which is incorporated herein by reference in its entirety. The excipient may have a glass transition temperatures (Tg) above about 35° C., preferably above about 40° C., more preferably above 45° C., most preferably above about 55° C.

Exemplary protein excipients include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline. Dispersibility—enhancing peptide excipients include dimers, trimers, tetramers, and pentamers comprising one or more hydrophobic amino acid components such as those described above.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The pharmaceutical formulation may also include a buffer or a pH adjusting agent, typically a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine hydrochloride, or phosphate buffers.

The pharmaceutical formulation may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-β-cyclodextrin and sulfobutylether-β-cyclodextrin), polyethylene glycols, and pectin.

The pharmaceutical formulation may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), both of which are incorporated herein by reference in their entireties.

"Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size. "Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

In one version, the powdered formulation for use in the present invention includes a dry powder having a particle size selected to permit penetration into the alveoli of the lungs, that is, less than 20 µm mass median diameter (MMD), preferably less than 10 µm, more preferably less than 7.5 µm, and most preferably less than 5 µm, and usually being in the range of 0.1 µm to 5 µm in diameter. The delivered dose efficiency (DDE) of these powders may be greater than 30%, more preferably greater than 40%, more preferably greater than 50% and most preferably greater than 60% and the aerosol particle size distribution is about 1.0-5.0 µm mass median aerodynamic diameter (MMAD), usually 1.5-4.5 µm MMAD and preferably 1.5-4.0 µm MMAD. These dry powders generally have a moisture content below about 10% by weight, usually below about 5% by weight, and preferably below about 3% by weight. Such powders are described in WO 95/24183, WO 96/32149, WO 99/16419, and WO 99/16422, all of which are all incorporated herein by reference in their entireties. Large, light particles also suitable for use in an aerosolization apparatus according to the invention are disclosed in U.S. Pat. Nos. 5,874,064; 5,985,309; and 6,503,480, all of which are incorporated herein by reference in their entireties.

Although the detailed description describes a preferred embodiment directed to spray drying, it is to be understood that the technology of the present invention can be used in other ways to produce particles or aerosolize liquid particles. For example, the apparatus and methods of the present invention can be used in combination with devices of the type disclosed in U.S. Pat. Nos. 5,845,846; 5,938,117; 6,014,970; and 6,352,209, all of which are incorporated herein by reference in their entireties, to produce the aerosolized spray of liquid feed stocks as disclosed therein. The apparatus and methods of the present invention can also be used in a variety of methods known in the art to produce particles from a liquid feed stock. For example, the present invention can be used in super critical fluid processing techniques as disclosed in U.S. Pat. No. 5,851,453, hereby incorporated in its entirety by reference, and with spray congealing methods as disclosed in U.S. Pat. No. 5,727,333, hereby incorporated in its entirety by reference.

Although the present invention has been described in considerable detail with regard to certain preferred versions thereof, other versions are possible, and alterations, permutations and equivalents of the version shown will become apparent to those skilled in the art upon a reading of the specification and study of the drawings. For example, the specific arrangement or shape of the components may be altered. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

What is claimed is:

1. A method for producing particles comprising:
   providing an atomizer comprising:
      a first annular channel for a liquid flow, wherein said first annular channel comprises a constriction having a diameter less than 0.51 mm for spreading a liquid into a thin film in the channel; and
      a first circular gas flow channel and a second annular channel for an atomizing gas flow, wherein said first and second annular channels are concentric, wherein said first annular channel is intermediate to the first circular gas flow channel and the second annular channel, and wherein said first circular gas flow channel and said second annular channel are positioned so that the atomizing gas impinges the liquid thin film to produce droplets at an impingement point downstream from a contact point between the liquid thin film and gas from the second annular channel;

a third gas flow channel in fluid communication with and perpendicular to said first circular gas flow channel at the impingement point, wherein a flow of gas exiting the third gas flow channel impinges the liquid thin film;

providing a drying chamber to dry the droplets to produce particles;

providing a collector to collect the dried particles; and atomizing a liquid feedstock with the atomizer, drying the droplets produced thereby with the drying chamber, and collecting the dried particles with the collector.

2. The method of claim 1, wherein the dried particles have a rugosity above 2.

3. The method of claim 1, wherein the dried particles have a density below 0.5 g/cm$^3$.

4. The method of claim 1, wherein the dried particles have a mass median diameter less than 20 μm.

5. The method of claim 1, wherein the liquid feedstock comprises an active pharmaceutical agent and at least one excipient.

6. The method of claim 5, wherein the excipient has a glass transition temperature above 35° C.

* * * * *